(12) United States Patent
Andersen et al.

(10) Patent No.: US 6,271,010 B1
(45) Date of Patent: Aug. 7, 2001

(54) CYCLOMALTODEXTRIN GLUCANOTRANSFERASE VARIANTS

(75) Inventors: Carsten Andersen, Vaerlose; Bjarne Rønfeldt Nielsen, Virum, both of (DK); Lubbert Dijkhuizen; Bauke Dijkstra, both of NN Haren (NL)

(73) Assignee: Novzymes A/S, Bagsvard (DE)

( * ) Notice: Subject to any disclaimer, the term of this patent is extended or adjusted under 35 U.S.C. 154(b) by 0 days.

(21) Appl. No.: 09/158,216

(22) Filed: Sep. 22, 1998

Related U.S. Application Data (60) Provisional application No. 60/062,659, filed on Oct. 8, 1997.

(30) Foreign Application Priority Data

Sep. 24, 1997 (DK) .................................... 1098/97

(51) Int. Cl.$^7$ ................ C12N 9/00; C12N 9/10; C12N 15/00; C07H 21/04
(52) U.S. Cl. ................ 435/193; 435/183; 435/320.1; 435/440; 536/232; 935/22
(58) Field of Search ................ 435/193, 320.1, 435/440, 183; 536/232

(56) References Cited

FOREIGN PATENT DOCUMENTS

WO 96/33267   10/1996   (WO).

*Primary Examiner*—Ponnathapura Achutamurthy
*Assistant Examiner*—Manjunath N. Rao
(74) *Attorney, Agent, or Firm*—Elias J. Lambiris; Jason I. Garbell (57) ABSTRACT

The present invention relates to variants of cyclomaltodextrin glucanotransferase of increased product specificity.

23 Claims, 4 Drawing Sheets

SEQUENCE LISTING

<160> NUMBER OF SEQ ID NOS: 2

<210> SEQ ID NO: 1
<211> LENGTH: 36
<212> TYPE: DNA
<213> ORGANISM: Artificial Sequence
<220> FEATURE:
<223> OTHER INFORMATION: oligonucleotide primers

<400> SEQUENCE: 1
cgtaacttat ttcatttagc agatctaaat caacag        36

<210> SEQ ID NO: 2
<211> LENGTH: 30
<212> TYPE: DNA
<213> ORGANISM: Artificial Sequence
<220> FEATURE:
<223> OTHER INFORMATION: oligonucleotide primers

<400> SEQUENCE: 2
gacaggcaat ggacgtcctt ataatagagc        30

CYCLOMALTODEXTRIN GLUCANOTRANSFERASE VARIANTS

CROSS-REFERENCE TO RELATED APPLICATIONS

This application claims priority under 35 U.S.C. 119 of Danish application 1098/97 filed Sep. 24, 1997 and U.S. Provisional application No. 60/062,659 filed on Oct. 8, 1997, the contents of which are fully incorporated herein by reference.

TECHNICAL FIELD

The present invention relates to variants of cyclomaltodextrin glucanotransferase of increased product specificity.

BACKGROUND ART

Cyclomaltodextrin glucanotransferase (E.C. 2.4.1.19), also designated cyclodextrin glucanotransferase or cyclodextrin glycosyltransferase, in the following termed CGTase, catalyses the conversion of starch and similar substrates into cyclomaltodextrins via an intramolecular transglycosylation reaction, thereby forming cyclomaltodextrins, in the following termed cyclodextrins (or CD), of various sizes. Commercially most important are cyclodextrins of 6, 7 and 8 glucose units, which are termed α-, β- and γ-cyclodextrins, respectively. Commercially less important are cyclodextrins of 9, 10, and 11 glucose units, which are termed δ-, ε-, and ζ-cyclodextrins, respectively. Cyclodextrins are thus cyclic glucose oligomers with a hydrophobic internal cavity. They are able to form inclusion complexes with many small hydrophobic molecules in aqueous solutions, resulting in changes in physical properties, e.g. increased solubility and stability and decreased chemical reactivity and volatility. Cyclodextrins find applications particularly in the food, cosmetic, chemical and pharmaceutical industries.

Most CGTases have both starch-degrading activity and transglycosylation activity. Although some CGTases produce mainly α-cyclodextrins and some CGTases produce mainly β-cyclodextrins, CGTases usually form a mixture of α-, β- and γ-cyclodextrins. Selective precipitation steps with organic solvents may be used for the isolation of separate α-, β- and γ-cyclodextrins. To avoid expensive and environmentally harmful procedures, the availability of CGTases capable of producing an increased ratio of one particular type of cyclodextrin, in particular with respect to α-, β- or γ-cyclodextrin, is desirable.

WO 96/33267 (Novo Nordisk) describes CGTase variants showing a modified substrate binding and/or product selectivity. Although CGTase variants produced by mutation at positions 47, 145, 146, 147, 196 or 371 have been described, the specific CGTase variants of this invention have never been described or even suggested.

SUMMARY OF THE INVENTION

The present invention provided novel CGTase variants of increased product specificity. Although CGTase variants of increased product specificity have been described in the prior art (WO 96/33267), the CGTase variants of the present invention have never been described or suggested.

Among the tremendous number of possible CGTase variants we have now succeeded in finding a limited number of variants showing increased product specificity when compared to the wild-type enzyme.

Accordingly the invention provides a CGTase variant of increased product specificity, in which one or more of the amino acid residues corresponding to the following positions have been introduced by substitution and/or insertion (CGTase Numbering):

(i) Position 47: 47C; 47D; 47E; 47F; 47G; 47I; 47K; 47N; 47P; 47R; 47S; 47T; 47V; 47W; or 47Y;
(ii) Position 145: 145D; 145H; 145I; 145N; 145Q; or 145V;
(iii) Position 146: 146H; 146K; 146L; 146T; 146V; or 146Y;
(iv) Position 147: 147C; 147D; 147E; 147N; 147Q;
(v) Position 196: 196C; 196E; 196F; 196G; 196H; 196I; 196K; 196L; 196M; 196P; 196Q; 196R; 196T; 196V; or 196W; 196Y and/or
(vi) Position 371: 371C; 371E; 371F; 371H; 371I; 371K; 371L; 371M; 371Q; 371R; 371T; 371V; or 371W.

Amino Acids

In the context of this invention the following symbols and abbreviations for amino acids and amino acid residues are used:

| A | = | Ala | = | Alanine |
|---|---|-----|---|---------|
| C | = | Cys | = | Cysteine |
| D | = | Asp | = | Aspartic acid |
| E | = | Glu | = | Glutamic acid |
| F | = | Phe | = | Phenylalanine |
| G | = | Gly | = | Glycine |
| H | = | His | = | Histidine |
| I | = | Ile | = | Isoleucine |
| K | = | Lys | = | Lysine |
| L | = | Leu | = | Leucine |
| M | = | Met | = | Methionine |
| N | = | Asn | = | Asparagine |
| P | = | Pro | = | Proline |
| Q | = | Gln | = | Glutamine |
| R | = | Arg | = | Arginine |
| S | = | Ser | = | Serine |
| T | = | Thr | = | Threonine |
| V | = | Val | = | Valine |
| W | = | Trp | = | Tryptophan |
| Y | = | Tyr | = | Tyrosine |
| B | = | Asx | = | Asp or Asn |
| Z | = | Glx | = | Glu or Gln |
| X | = | Xaa | = | Any amino acid |
| * | = | Deletion or absent amino acid | | |

CGTase Variants

A CGTase variant of this invention is a CGTase variant or mutated CGTase, having an amino acid sequence not found in nature.

A CGTase variant or mutated CGTase of this invention may be considered a functional derivative of a precursor CGTase enzyme (i.e. the native, parental, or wild-type enzyme), and may be obtained by alteration of a DNA nucleotide sequence of a precursor gene or its derivatives, encoding the precursor enzyme.

The CGTase variant or mutated CGTase may be expressed and produced when the DNA nucleotide sequence encoding the CGTase variant is inserted into a suitable vector in a suitable host organism. The host organism is not necessarily identical to the organism from which the precursor gene originated.

In the literature, enzyme variants have also been referred to as mutants or muteins.

CGTase Numbering

In the context of this invention a specific numbering of amino acid residue positions in CGTase enzymes is employed. By alignment of the amino acid sequences of various known CGTases it is possible to unambiguously allot a CGTase amino acid position number to any amino acid residue position in any CGTase enzyme, which amino acid sequence is known.

Using the numbering system originating from the amino acid sequence of the CGTase obtained from *Bacillus circu-*

*lans* Strain 251, aligned with the amino acid sequence of a number of other known CGTases, it is possible to indicate the position of an amino acid residue in a CGTase enzyme unambiguously.

This CGTase Numbering system has been described in WO 96/33267, see Table 1, pages 9–31 (in which table *Bacillus circulans* Strain 251 is represented as a). Table 1 of WO 96/33267 also shows the protein sequences of a number of relevant CGTase and is hereby incorporated by reference.

In describing the various CGTase variants produced or contemplated according to the invention, the following nomenclatures are adapted for ease of reference:
[Original Amino Acid; Position; Substituted Amino Acid]
Accordingly, the substitution of serine with alanine in position 145 is designated as S145A.

Amino acid residues which represent insertions in relation to the amino acid sequence of the CGTase from *Bacillus circulans* Strain 251, are numbered by the addition of letters in alphabetical order to the preceding CGTase number, such as e.g. position 91aF for the "insert" Phe between Thr at position 91 and Gly at position 92 of the amino acid sequence of the CGTase from Thermoanaerobacter sp. ATCC 53627, cf. Table 1 (j).

Deletion of a proline at position 149 is indicated as P149*, and an insertion between position 147 and 148 where no amino acid residue is present, is indicated as *147aD for insertion of an aspartic acid in position 147a.

Multiple mutations are separated by slash marks ("/"), e.g. S145A/D147L, representing mutations in positions 145 and 147 substituting serine with alanine and aspartic acid with leucine, respectively.

If a substitution is made by mutation in e.g. a CGTase derived from a strain of *Bacillus circulans*, the product is designated e.g. "*B. circulans*/S145A".

All positions referred to in this application by CGTase numbering refer to the CGTase numbers described above.

BRIEF DESCRIPTION OF THE DRAWINGS

The present invention is further illustrated by reference to the accompanying drawing, in which.

DETAILED DISCLOSURE OF THE INVENTION

The present invention provides novel CGTase variants, i.e. CGTase variants having an amino acid sequence not found in nature.

Formally, the CGTase variant of the invention may be regarded as a functional derivative of a precursor CGTase enzyme (i.e. the native, parental, or wild-type enzyme), by substitution, insertion and/or deletion of one or more amino acid residue(s) of the precursor enzyme.

In the context of this invention, a CGTase variant of increased product specificity is a CGTase variant capable of producing an increased ratio of one particular type of cyclodextrin, when compared to the wild-type enzyme.

In a CGTase variant of the invention, one or more amino acid residues corresponding to the following positions (CGTase Numbering) have been introduced by substitution and/or insertion:

(i) Position 47: 47C; 47D; 47E; 47F; 47G; 47I; 47K; 47N; 47P; 47R; 47S; 47T; 47V; 47W; or 47Y;
(ii) Position 145: 145D; 145H; 145I; 145N; 145Q; or 145V;
(iii) Position 146: 146H, 146K; 146L; 146T; 146V; or 146Y;
(iv) Position 147: 147C; 147D; 147E; 147N; 147Q;
(v) Position 196: 196C; 196E; 196F; 196G; 196H; 196I; 196K; 196L; 196M; 196P; 196Q; 196R; 196T; 196V; 196W; or 196Y and/or
(vi) Position 371: 371C; 371E; 371F; 371H; 371I; 371K; 371L; 371M; 371Q; 371R; 371T; 371V; or 371W.

In a preferred embodiment, CGTase variants showing an increased product specificity with respect to the production of α-cyclodextrin are provided, in which variants one or more of the amino acid residues corresponding to the following positions have been introduced by substitution and/or insertion (CGTase Numbering):

(i) Position 47: 47F; 47K; 47R; 47W; or 47Y;
(ii) Position 145: 145D; 145H; 145N; or 145Q;
(iii) Position 146: 146H, 146K; 146L; 146T; 146V; or 146Y;
(iv) Position 147: 147C; 147D; 147E; 147N; 147Q;
(v) Position 196: 196C; 196E; 196F; 196G; 196H; 196I; 196K; 196L; 196M; 196P; 196Q; 196R; 196T; 196V; 196W; or 196Y and/or
(vi) Position 371: 371C; 371H; 371K; 371R; or 371T.

In another preferred embodiment, CGTase variants showing an increased product specificity with respect to the production of β-cyclodextrin are provided, in which variants one or more of the amino acid residues corresponding to the following positions have been introduced by substitution and/or insertion (CGTase Numbering):

(i) Position 47: 47C; 47D; 47E; 47F; 47G; 47I; 47N; 47P; 47S; 47T; 47V; 47W; or 47Y;
(ii) Position 145: 145D; 145I; 145N; or 145V;
(iii) Position 147: 147E;
(iv) Position 196: 196C; 196E; 196F; 196G; 196H; 196I; 196K; 196L; 196M; 196P; 196Q; 196R; 196T; 196V; 196W; or 196Y and/or
(v) Position 371: 371C; 371E; 371F; 371H; 371I; 371K; 371L; 371M; 371Q; 371R; 371T; 371V; or 371W.

In yet another preferred embodiment, CGTase variants showing an increased product specificity with respect to the production of γ-cyclodextrin are provided, in which variants one or more of the amino acid residues corresponding to the following positions have been introduced by substitution and/or insertion (CGTase Numbering):

(i) Position 47: 47C; 47D; 47E; 47F; 47G; 47I; 47N; 47P; 47S; 47T; 47V; 47W; or 47Y;
(ii) Position 145: 145D; 145I; 145N; or 145V;
(iii) Position 147: 147E;
(iv) Position 196: 196C; 196E; 196F; 196G; 196H; 196I; 196K; 196L; 196M; 196P; 196Q; 196R; 196T; 196V; 196W; or 196Y and/or
(v) Position 371: 371C; 371E; 371F; 371H; 371K; 371M; 371Q; 371R; 371T; or 371W.

The CGTase variant of the invention may be derived from any CGTase enzyme found in nature. However, the CGTase variant of the invention preferably is derived from a microbial enzyme, preferably a bacterial enzyme, and preferably the CGTase variant is derived from a strain of Bacillus, a strain of Brevibacterium, a strain of Clostridium, a strain of Corynebacterium, a strain of Klebsiella, a strain of Micrococcus, a strain of Thermoanaerobium, a strain of Thermoanaerobacter, a strain of Thermoanaerobacterium, a strain of Thermoanaerobacterium, or a strain of Thermoactinomyces.

In a more preferred embodiment, the CGTase variant of the invention is derived from a strain of *Bacillus autolyticus*, a strain of *Bacillus cereus*, a strain of *Bacillus circulans*, a strain of *Bacillus circulans* var. *alkalophilus*, a strain of *Bacillus coagulans*, a strain of *Bacillus firmus*, a strain of *Bacillus halophilus*, a strain of *Bacillus macerans*, a strain of *Bacillus megaterium*, a strain of *Bacillus ohbensis*, a strain of *Bacillus stearothermophilus*, a strain of *Bacillus subtilis*, a strain of *Klebsiella pneumonia*, a strain of *Thermoanaerobacter ethanolicus*, a strain of *Thermoanaerobacter finnii*, a strain of *Clostridium thermoamylolyticum*, a strain of *Clostridium thermosaccharolyticum*, or a strain of *Thermoanaerobacterium thermosulfurigenes*.

In a most preferred embodiment, the CGTase variant of the invention is derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, the strain *Bacillus circulans* Strain 251, or the strain Thermoanaerobacter sp. ATCC 53627, or mutants or variants thereof.

If the CGTase variant of the invention is derived from a strain of *Bacillus circulans*, one or more of the amino acid residues corresponding to the following positions may be introduced:
(i) Position R47: R47C; R47D; R47E; R47F; R47G; R47I; R47K; R47N; R47P; R47S; R47T; R47V; R47W; or R47Y;
(ii) Position S145: S145D; S145H; S145I; S145N; S145Q; or S145V;
(iii) Position S146: S146H, S146K; S146L; S146T; S146V; or S146Y;
(iv) Position D147: D147C; D147E; D147N; D147Q;
(v) Position D196: D196C; D196E; D196F; D196G; D196H; D196I; D196K; D196L; D196M; D196P; D196Q; D196R; D196T; D196V; D196W; or D196Y and/or
(vi) Position D371; D371C; D371E; D371F; D371H; D371I; D371K; D371L; D371M; D371Q; D371R; D371T; D371V; or D371W.

Preferably the CGTase variant is derived from *Bacillus circulans* Strain 251, or a mutant or a variant thereof.

If the CGTase variant is derived from a strain of Thermoanaerobacter sp., one or more of the amino acid residues corresponding to the following positions may be introduced:
(i) Position K47; K47C; K47D; K47E; K47F; K47G; K47I; K47N; K47P; K47R; K47S; K47T; K47V; K47W; or K47Y;
(ii) Position S145: S145D; S145H; S145I; S145N; S145Q; or S145V;
(iii) Position E146: E146H, E146K; E146L; E146T; E146V; or E146Y;
(iv) Position T147: T147C; T147D; T147E; T147N; T147Q;
(v) Position D196: D196C; D196E; D196F; D196G; D196H; D196I; D196K; D196L; D196M; D196P; D196Q; D196R; D196T; D196V; D196W; or D196Y and/or
(vi) Position D371: D371C; D371E; D371F; D371H; D371I; D371K; D371L; D371M; D371Q; D371R; D371T; D371V; or D371W.

Preferably the CGTase variant is derived from the strain Thermoanaerobacter sp. ATCC 53627, or a mutant or a variant thereof.

Example 1 describes the construction of *T. thermosulfurigenes* CGTase variants Asp196His (D196H) and Asp371Arg (D371R) with modified product specificity, in which site-directed mutagenesis has lead to an altered number of hydrogen bonds in the subsite of the active site cleft. The variants are derived from a *Thermoanaerobacter thermosulfurigenes* EM1 CGTase (i.e. the wild-type), obtained as described by Haeckel and Bahl [Haeckel, K., and Bahl, H. (1989) *FEMS Microbiol. Lett.* 60, 333–338 or Knegtel R. M. A., Wind R. D., Rozeboom H. J., Kalk K. H., Buitelaar R. M., Dijkhuizen L., Dijkstra B. W. J. Mol. Biol. 256:611–622 (1996)].

In another preferred embodiment, the CGTase variant of the invention comprises one or more of the following amino acid residues (CGTase Numbering):
(i) 47K/145E/146V/147N;
(ii) 47K/145E/146E/147N;
(iii) 47K/145D/146R/147D;
(iv) 47K/145D/146E/147D;
(v) 47K/145E/146V/147N/196H;
(vi) 47K/145E/146E/147N/196H;
(vii) 47K/145E/146V/147N/196H/371R;
(viii) 47K/145E/146E/147N/196H/371R;
(ix) 47K/145D/146R/147D/196H;
(x) 47K/145D/146E/147D/196H;
(xi) 47K/145D/146R/147D/196H/371R; and/or
(xii) 47K/145D/146R/147D/196H/371R.
(xiii) 47K/196H;
(xiv) 47R/196H
(xv) 145E/146V/147N;
(xvi) 145E/146E/147N;
(xvii) 145D/146R/147D;
(xviii) 145D/146E/147D;
(xix) 47K/371R;
(xx) 47R/371R;

If the CGTase variant is derived from a strain of *Bacillus circulans* one or more of the following amino acid residues may be introduced:
(i) R47K/S145E/S146V/D147N;
(ii) R47K/S145E/S146E/D147N;
(iii) R47K/S145D/S146R;
(iv) R47K/S145D/S146E;
(x) R47K/S145E/S146V/D147N/D196H;
(vi) R47K/S145E/S146E/D147N/D196H;
(vii) R47K/S145E/S146V/D147N/D196H/D371R;
(viii) R47K/S145E/S146E/D147N/D196H/D371R;
(ix) R47K/S145D/S146R/D196H;
(x) R47K/S145D/S146E/D196H;
(xi) R47K/S145D/S146R/D196H/D371R;
(xii) R47K/S145D/S146R/D196H/D371R.
(xiii) R47K/D196H;
(xiv) S145E/S146V/D147N;
(xv) S145E/S146E/D147N;
(xvi) S145D/S146R;
(xvii) S145D/S146E;
(xviii) R47K/D371R;

Preferably the CGTase variant is derived from *Bacillus circulans* Strain 251, or a mutant or a variant thereof.

If the CGTase variant is derived from a strain of Thermoanaerobacter sp., one or more of the following amino acid residues may be introduced:
(i) S145E/E146V/T147N;
(ii) S145E/T147N;
(iii) S145D/E146R/T147D;
(iv) S145D/T147D;
(x) S145E/E146V/T147N/D196H;
(vi) S145E/T147N/D196H;
(vii) S145E/E146V/T147N/D196H/D371R;
(viii) S145E/T147N/D196H/D371R;
(ix) S145D/E146R/T147D/D196H;
(x) S145D/T147D/D196H;
(xi) S145D/E146R/T147D/D196H/D371R;
(xii) S145D/E146R/T147D/D196H/D371R.
(xiii) S145E/E146V/T147N;

(xiv) S145E/T147N;
(xv) S145D/E146R/T147D;
(xvi) S145D/T147D; and/or
(xvii) K47R/D371R;
(xviii) K47R/D196H Preferably the CGTase variant is derived from the strain Thermoanaerobacter sp. ATCC 53627, or a mutant or a variant thereof.

In a further aspect the invention relates to the use of a CGTase variant of the invention for increasing the α or β or γ-cyclodextrin content of the final cyclodextrin product of cyclodextrins processes.

In a final aspect the invention relates to a method of increasing the product specificity with respect to the production of α or β or γ-cyclodextrins, wherein one or more amino acid residues, corresponding to the positions of the CGTase variants of the invention mentioned above, have been introduced by substitution and/or insertion.

EXAMPLES

Example 1
Construction of *T. thexmosulfurigenes* CGTase Variants With Modified Product Specificity
Bacterial Strains, Plasmids And Growth Conditions

*Escherichia coli* JM109 [endA1 recA1 gyrA96 thi hsdR17 (rK–,mK+) relA1 supE44 (lac-proAB) [F' traD36 proAB lacIqZ M15] (Yanish-Perron et al. 1985 *Gene* 33, 103–119) was used for recombinant DNA manipulations. *Escherichia Coli* PC1990 (Lazzaroni and Portalier 1979 *FEMS Microbiol. Lett.* 5, 411–416), known to leak periplasmic proteins into the supernatant because of a mutation in its tolB locus, was used for production of CGTase (mutant) proteins. Plasmid pCT2, a derivative of pUC18 containing the amyA gene of *Thermoanaerobacterium thermosulfurigenes* EM1 (Knegtel R. M. A., Wind R. D., Rozeboom H. J., Kalk K. H., Buitelaar R. M., Dijkhuizen L., Dijkstra B. W. J. Mol. Biol. 256:611–622 (1996)), was used for site-directed mutagenesis, sequencing and expression of the CGTase (mutant) proteins. Plasmid-carrying bacterial strains were grown on LB medium in the presence of 100 μg/ml ampicillin. When appropriate, IPTG (isopropyl-β-D-thiogalactopyranoside) was added at a concentration of 0.1 mM for induction of protein expression.

DNA Manipulations

DNA manipulations and transformation of *E. coli* were essentially as described by Sambrook et al. [Sambrook, J., Fritsch, E. J., and Maniatis, T. (1989) *Molecular cloning: a laboratory manual*, Cold Spring Harbor Laboratory Press, New York]. Transformation of *E. coli* by electroporation was performed using the Bio-Rad gene pulser apparatus (Bio-Rad, Veenendaal, The Netherlands) The selected conditions were 2.5 kV, 25 μF and 200Ω.

Site-directed Mutagenesis

Mutant CGTase genes were constructed via a double PCR method using the Pfu DNA polymerase from Stratagene (Westburg, Leusden, The Netherlands). A first PCR reaction was carried out with the mutagenesis primer for the coding strand plus a primer 195–715 bp downstream on the template strand. The reaction product was subsequently used as primer in a second PCR reaction together with a primer 295–815 bp upstream on the coding strand. The product of the last reaction was cut with NcoI and MunI, and exchanged with the corresponding fragment (900 bp) from the vector pCT2. The resulting (mutant) plasmid was transformed to *E. coli* JM109 for sequencing and *E. coli* PC1990 for production of the (mutant) proteins. The following oligonucleotides were used:

D196H 5'-CGTAACTTATTTCATTTAGC
 AGATCTAAATCAACAG-3'  (SEQ ID No. 1)

D371R 5'-GACAGGCAATGGACGTCCTTATAA
 TAGAGC-3'  (SEQ ID NO. 2).

Successful mutations resulted in the underlined restriction sites (BglII for D196H and AatII for D371R), which allowed quick screening of transformants. Mutations were verified by DNA sequencing (Sanger et al. 1977 *Proc. Natl. Sci. USA* 74, 5463–5467). All 900 bp on the MunI-NcoI fragment obtained by PCR were checked by DNA-sequencing.

Production And Purification of CGTase Proteins

For production of CGTase proteins, *E. coli* PC1990 was grown in a 2-liter fermentor at pH 7.0 and 30 C. The medium contained 2% (w/w) tryptone (Oxoid, Boom BV, Meppel, The Netherlands), 1% (w/w) yeast extract (Oxoid), 1% (w/w) sodium chloride, 1% (w/w) casein hydrolysate (Merck, Darmstadt, Germany), 100 μg/l ampicillin and 0.1 mM IPTG. Growth was monitored by measuring the optical density at 450 nm. When the optical density at 450 nm reached 2 to 3, an extra amount of 50 g tryptone was added to the fermentor. Cells were harvested after 20–24 hours of growth (8,000 g, 30 minutes, 4° C.), at an optical density of 8–12, and the supernatant was used for further purification of the CGTases. Supernatant was directly applied to an α-CD-sepharose-6FF affinity column (Monma et al. 1988 *Biotechnol. Bioeng.* 32, 404–407). After washing the column with 10 mM sodium acetate (pH 5.5), the CGTase was eluted with the same buffer supplemented with 1% (w/w) α-CD. Purity and molecular weight of the CGTase (mutant) proteins were checked on SDS-PAGE (Wind et al. 1995 *Appl. Environ. Microb.* 61, 1257–1265). Protein concentrations were determined by the method of Bradford, using the Coomassie protein assay reagent of Pierce (Pierce Europe bv, Oud-Beijerland, The Netherlands).

Enzyme Assays

All assays were standardly performed at pH 6.0 and 50° C. Cyclization and saccharifying assays were performed as described by Penninga et al. (Penninga, D., Strokopytov, B., Rozeboom, H. J., Lawson, C. L., Dijkstra, B. W., Bergsma, J., and Dijkhuizen, L. (1995) *Biochemistry* 34, 3368–3376). Units for the different reactions were defined as the amount of enzyme producing 1 μmol of substrate at pH 6.0 and 50° C.

HPLC Product Analysis

Formation of cyclodextrins was measured under industrial process conditions by incubation of 0.1 U/ml CGTase (β-CD forming activity) with 10% Paselli WA4 (pregelatinized drum-dried starch with a high degree of polymerization; AVEBE, The Netherlands) in 10 mM sodium citrate buffer (pH 6.0) at 60° C. for 45 hours. Samples were taken at regular time intervals and boiled for 10 minutes. Products formed were analyzed by HPLC, using a 25-cm Econosil-NH2 10-μm column (Alltech Nederland bv, Breda, The Netherlands) eluted with acetonitrile-water (65:45) at 1 ml/minute. Products were detected by a refractive index detector (Waters 410, Waters Chromatography Division, Milford, USA). The temperature of the flow cell and column was set at 50° C., to avoid possible precipitation of starch. Formation of linear products was directly analyzed. Formation of CD's was analyzed after incubation of the samples with an appropriate amount of β-amylase (type I-B from Sweet potato, Sigma, Boom BV, Meppel, The Netherlands).

Cyclodextrin Product Specificity

Figure 1:
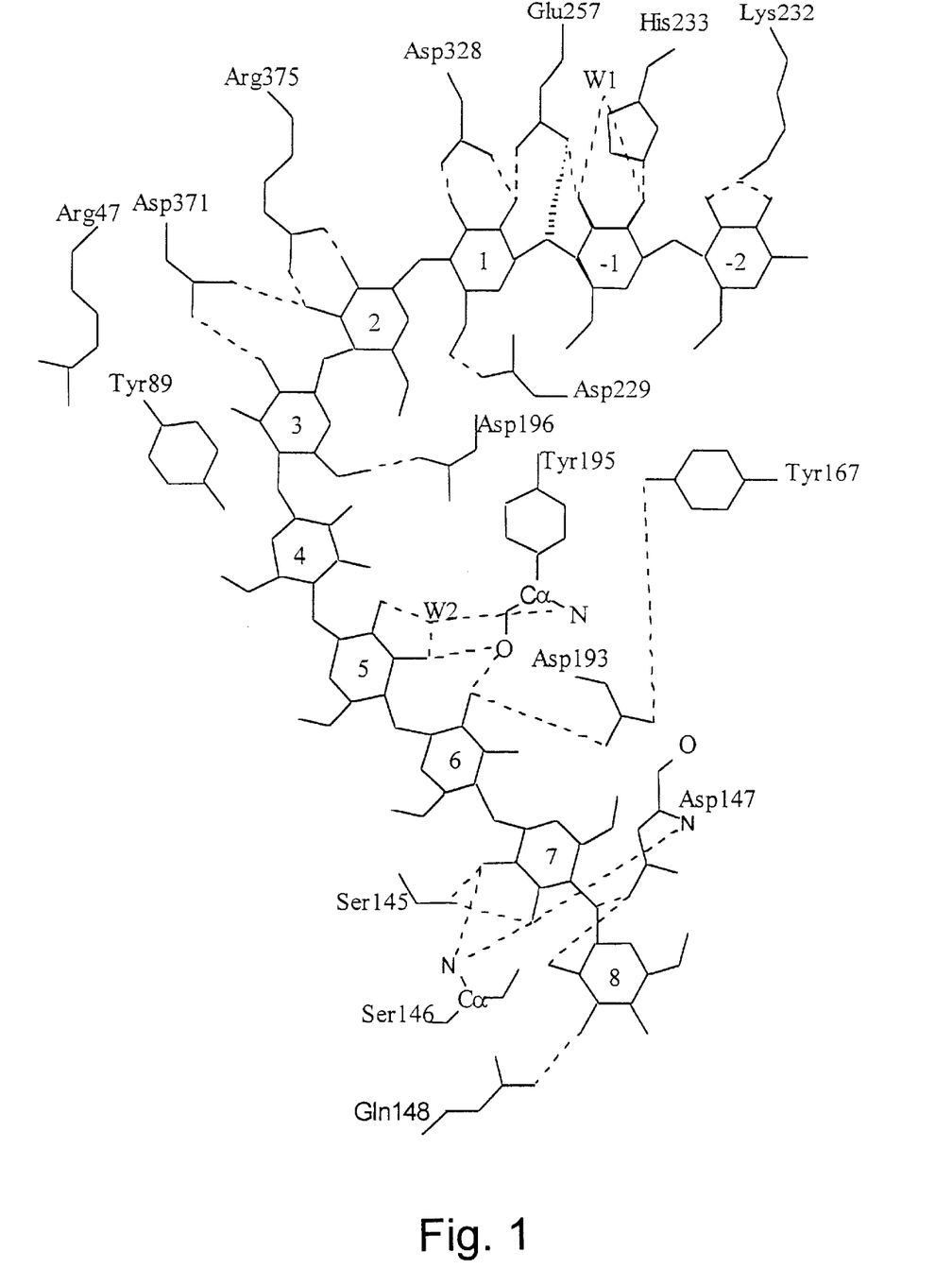
FIG. 1 shows a cartoon of the substrate binding cleft of *B. circulans* st. 251 CGTase. Dote lines indicate hydrogen bonds between the enzyme (water) and the substrate. Cleavage point is defined between glucose residue −1 and 1.
Figure 2:
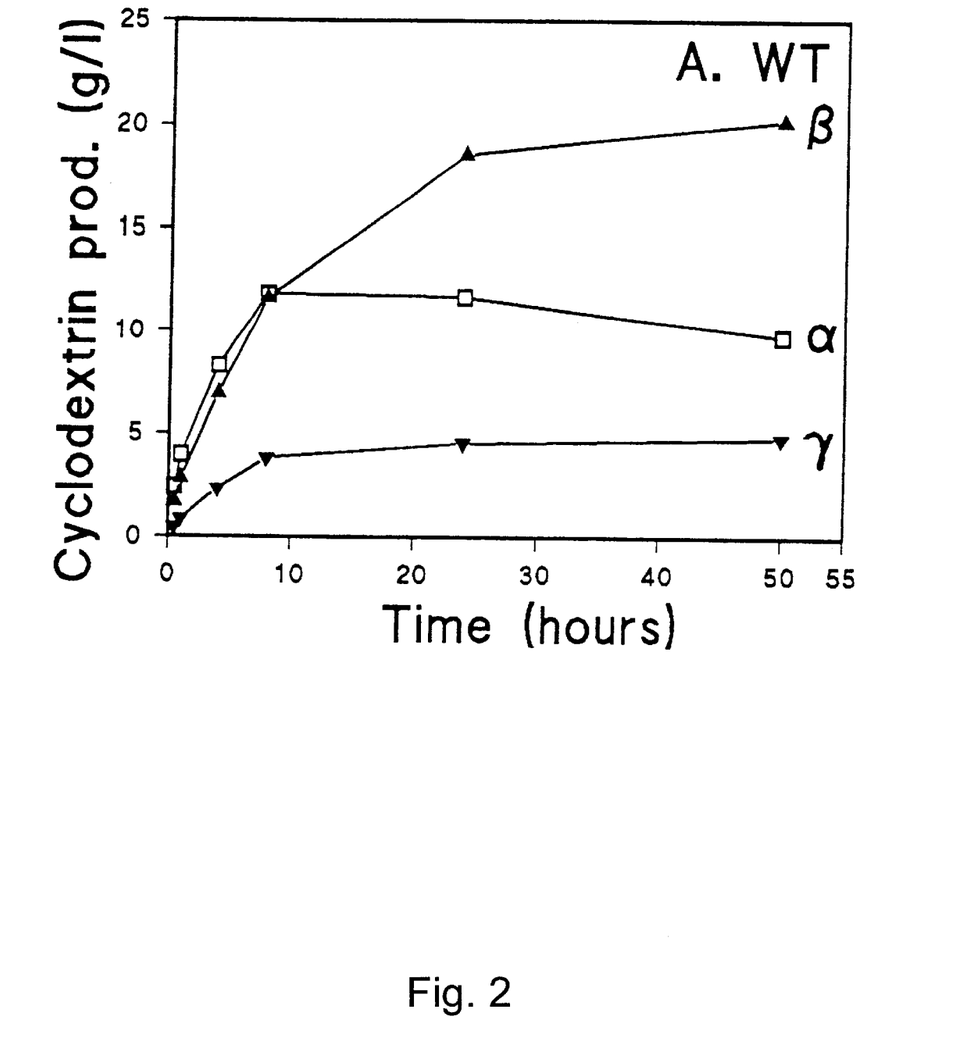
FIGS. 2, 3 and 4 show cyclodextrins formed during incubation of (mutant) CGTase proteins from *Thermoanaerobacterium thermosulfurigenes*. A. wild-type (FIG. 2); B. Variant D196H (FIG. 3); C. variant D371R (FIG. 4).
Figure 3:
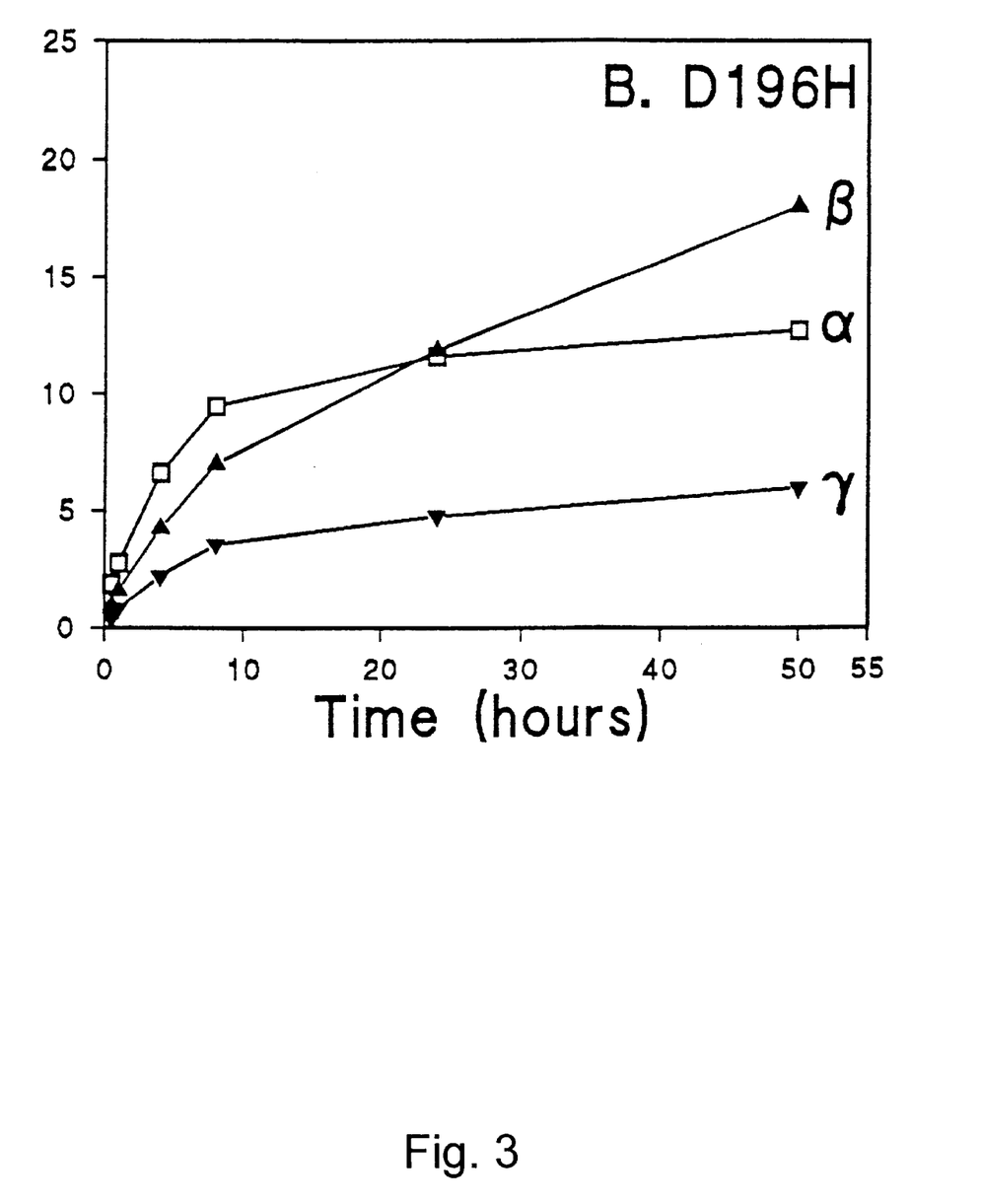
Figure 4:
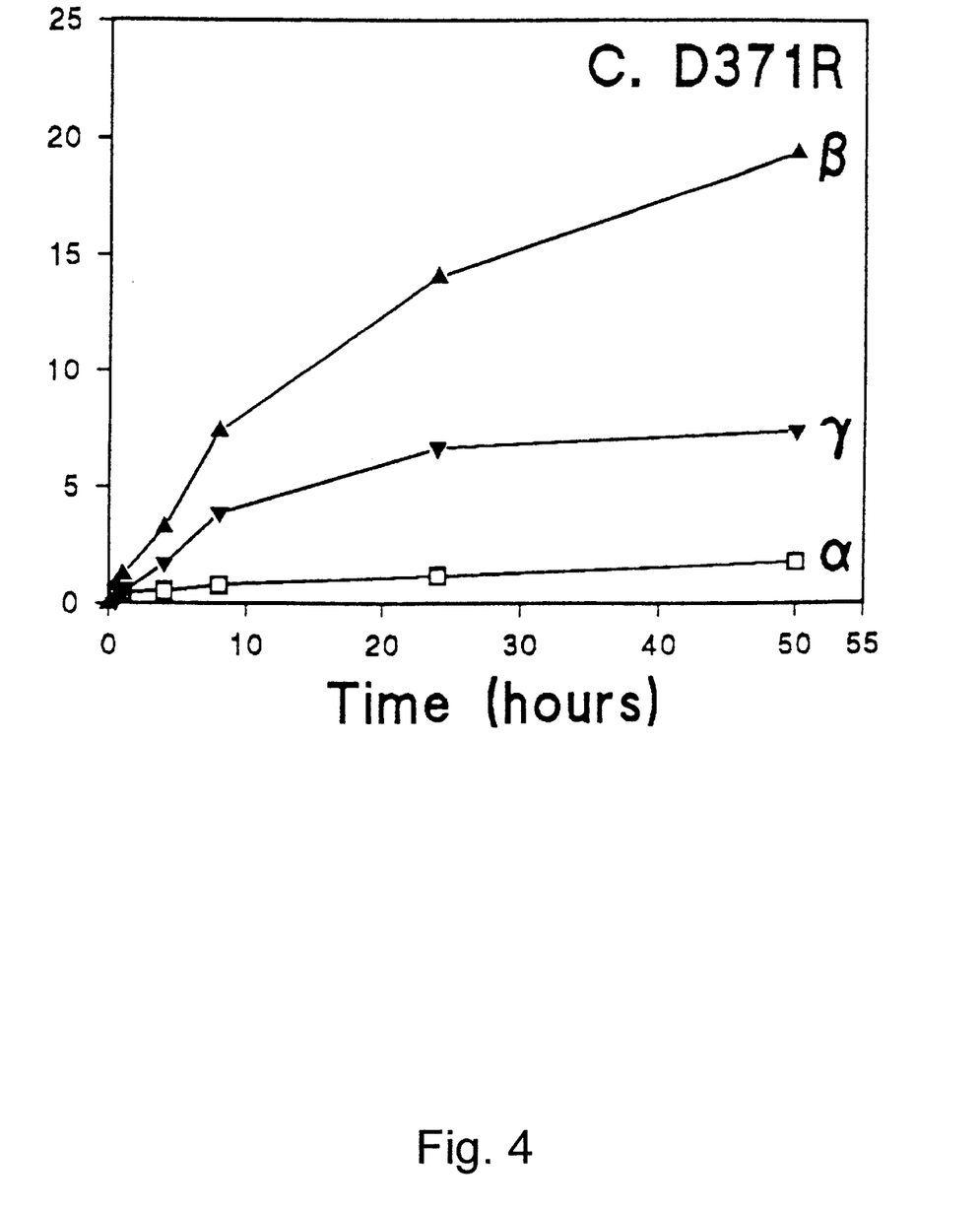

In order to change the product specificity of Thermoanaerobacterium CGTase, we replaced Asp196 by His (D196H) and Asp371 by Arg (D371R). In mutant D196H production of α-CD was increased at the expense of the production of β-CD when compared to the wild-type CGTase (FIG. 2). The cyclodextrin product ratio was changed from 28:58:14 (α:β:γ) for the wild-type CGTase to 35:49:16 for mutant D196H (Table 1). This is according to expectations on the basis of the structural work. By the replacement of Asp197 by His a larger residue is introduced, this would block the so-called straight substrate binding mode. Furthermore, His 197 is probably also able to form hydrogen bonds with the substrate bound in the 'bent' mode. These results lean more vigour to the theory that the bent conformation is correlated with α-cyclodextrin production, and show that it can be used to rationally engineer a CGTase with desired product specificity.

TABLE 1

| Cyclization | Product Ratio (%) | Conversion of Starch | | | |
|---|---|---|---|---|---|
| activity | (U/ml) | α | β | γ | into cyclodextrins (%) |
| Wild-type | 163 | 28 | 58 | 14 | 35 |
| D196H | 144 | 35 | 49 | 16 | 37 |
| D371R | 14 | 6 | 68 | 26 | 29 |

Starch conversion of *T. thermosulfurigenes* wild-type and mutant CGTase proteins. Proteins (0.1 U/ml β-CD forming activity) were incubated for 45 H at pH 6.0 and 60° C. with 10% Paselli WA4.

Asp 371 has a very important role in substrate binding at subsite 2, both in the BC251 and Tabium CGTase. Replacement of Asp371 by Arg resulted in the introduction of a very bulky amino acid, which would probably interfere severely with binding of all kinds of substrates at subsite 2, thereby explaining the overall decrease of activity. Apart from this low activity, the product ratio changed from 28:58:14 for the wild-type enzyme to 6:68:26 for mutant D371H (Table 1, FIG. 2). This suggests that the cyclisation reaction leading to a α-cyclodextrin is more hampered by the Arg 371 than the other cyclisation reactions. Probably this bulky residue is sterically hindering the 'bent' conformation. These results show that the Tabium CGTase can changed from a α/β-cyclodextrin producer to a β/γ-cyclodextrin producer by just one mutation, illustrating the feasibility of CGTase protein engineering.

The invention is further illustrated with reference to the following examples which are not intended to be in any way limiting to the scope of the invention as claimed.

What is claimed is:

1. A CGTase variant having an amino acid sequence which differs from the amino acid sequence of a parent CGTase, wherein the parent CGTase is a Thermoanaerobacter CGTase and the difference between the amino acid sequence of the CGTase variant and the amino acid sequence of the parent CGTase comprises one or more of the following:
  47C; 47D; 47E; 47F; 47G; 47I; 47K; 47N; 47P; 47S; 47T; 47V; 47W; 47Y;
  145D; 145H; 145I; 145N; 145Q; 145V;
  146H; 146L; 146T; 146V; 146Y;
  147C; 147E; 147N; 147Q;
  196C; 196E; 196F; 196H; 196I; 196K; 196M; 196P; 196Q; 196R; 196T; 196V; 196W; 196Y; and
  371C; 371F; 371H; 371K; 371M; 371R; 371T; 371W;
wherein each position corresponds to the position of the amino acid sequence of the mature CGTase obtained from *Bacillus circulans* strain 251.

2. The CGTase variant of claim 1, wherein the parent CGTase is a *Thermoanaerobacter thermosulfurigenes* CGTase.

3. The CGTase variant of claim 1, wherein the parent CGTase is a *Thermoanaerobacter ethanolicus* CGTase.

4. The CGTase variant of claim 1, wherein the parent CGTase is a *Thermoanaerobacter finnii* CGTase.

5. The CGTase variant of claim 1, wherein the parent CGTase is a CGTase obtained from strain ATCC 53627.

6. The CGTase variant of claim 1, wherein the difference comprises 47C; 47D; 47E; 47F; 47G; 47I; 47K; 47N; 47P; 47S; 47T; 47V; 47W; or 47Y.

7. The CGTase variant of claim 1, wherein the difference comprises 145D; 145H; 145I; 145N; 145Q; or 145V.

8. The CGTase variant of claim 1, wherein the difference comprises 146H, 146L; 146T; 146V; or 146Y.

9. The CGTase variant of claim 1, wherein the difference comprises 147C; 147E; 147N; or 147Q.

10. The CGTase variant of claim 1, wherein the difference comprises 196C; 196E; 196F; 196H; 196I; 196K; 196M; 196P; 196Q; 196R; 196T; 196V; 196W; or 196Y.

11. The CGTase variant of claim 10, wherein the difference comprises 196H.

12. The CGTase variant of claim 1, wherein the difference comprises 371C; 371F; 371H; 371K; 371M; 371R; 371T; or 371W.

13. The CGTase variant of claim 12, wherein the difference comprises D371R.

14. The CGTase variant of claim 1, wherein the difference comprises:
47K/145E/146V/147N;
47K/145E/146E/147N;
47K/145D/146R/147D;
47K/145D/146E/147D;
47K/145E/146V/147N/196H;
47K/145E/146E/147N/196H;
47K/145E/146V/147N/196H/371R;
47K/145E/146E/147N/196H/371R;
47K/145D/146R/147D/196H;
47K/145D/146E/147D/196H;
47K/145D/146R/147D/196H/371R;
47K/145D/146E/147D/196H/371R;
47K/196H;
47R/196H;
145E/146V/147N;
145E/146E/147N;
145D/146R/147D;
145D/146E/147D;
47K/371R; or
47R/371R.

15. The CGTase variant of claim 14, wherein the parent CGTase is a *Thermoanaerobacter thermosulfurigenes* CGTase.

16. The CGTase variant of claim 14, wherein the parent CGTase is a *Thermoanaerobacter ethanolicus* CGTase.

17. The CGTase variant of claim 14, wherein the parent CGTase is a *Thermoanaerobacter finnii* CGTase.

18. The CGTase variant of claim 1, wherein the difference comprises:
S145E/E146V/T147N;
S145E/T147N;
S145D/E146R/T147D;
S145D/T147D;
S145E/E146V/T147N/D196H;
S145E/T147N/D196H;
S145E/E146V/T147N/D196H/D371R;
S145E/T147N/D196H/D371R;
S145D/E146R/T147D/D196H;
S145D/T147D/D196H;
S145D/E146R/T147D/D196H/D371R;
S145D/E146R/T147D/D196H/D371R;
S145E/E146V/T147N;
S145E/T147N;
S145D/E146R/T147D;
S145D/T147D;
K47R/D371R; or
K47R/D196H.

19. The CGTase variant of claim 18, which is derived from the strain Thermoanaerobacter sp. ATCC 53627, or a mutant or a variant thereof.

20. A method of producing a cyclodextrin, comprising treating a starch with a CGTase variant of claim 1.

21. The method of claim 20, wherein the cyclodextrin is a α-cyclodextrin.

22. The method of claim 20, wherein the cyclodextrin is a β-cyclodextrin.

23. The method of claim 20, wherein the cyclodextrin is a γ-cyclodextrin.

* * * * *